United States Patent [19]
Shelton et al.

[11] Patent Number: 5,402,070
[45] Date of Patent: Mar. 28, 1995

[54] FAULT-TOLERANT ELECTIVE REPLACEMENT INDICATION FOR IMPLANTABLE MEDICAL DEVICE

[75] Inventors: Michael B. Shelton, Minneapolis; Ross O. Starkson, Woodbury; Craig L. Schmidt, Eagan; H. Toby Markowitz, Roseville, all of Minn.

[73] Assignee: Medtronic, Inc., Minneapolis, Minn.

[21] Appl. No.: 275,863

[22] Filed: Jul. 15, 1994

Related U.S. Application Data

[62] Division of Ser. No. 81,746, Jun. 22, 1993.

[51] Int. Cl.⁶ ............................................. A61N 1/378
[52] U.S. Cl. ..................................... 324/433; 607/29
[58] Field of Search ............... 324/426, 428, 429, 430, 324/432, 433; 607/29, 27

[56] References Cited

U.S. PATENT DOCUMENTS

| | | |
|---|---|---|
| 3,057,356 | 10/1992 | Greatbatch . |
| 3,478,746 | 11/1969 | Greatbatch . |
| 3,557,796 | 1/1971 | Keller . |
| 3,631,860 | 1/1972 | Lopin . |
| 3,805,796 | 4/1974 | Terry . |
| 3,833,005 | 9/1974 | Wingrove . |
| 3,857,399 | 12/1974 | Zacouto . |
| 3,865,119 | 2/1975 | Svensson . |
| 3,870,050 | 3/1975 | Greatbach . |
| 4,038,991 | 8/1977 | Walters . |
| 4,043,347 | 8/1977 | Renirie . |
| 4,049,003 | 9/1977 | Walters . |
| 4,049,004 | 9/1977 | Walters . |
| 4,066,086 | 1/1978 | Alferness . |
| 4,231,027 | 10/1980 | Mann . |
| 4,237,897 | 12/1980 | Beane . |
| 4,250,883 | 2/1981 | Thompson . |
| 4,259,639 | 3/1981 | Renirie . |
| 4,290,429 | 9/1981 | Blaser . |
| 4,324,251 | 4/1982 | Mann . |
| 4,340,062 | 7/1982 | Thompson . |
| 4,433,294 | 2/1984 | Windebank ................. 324/426 |
| 4,448,197 | 5/1984 | Nappholz . |
| 4,476,868 | 10/1984 | Thompson . |
| 4,556,063 | 12/1985 | Thompson . |
| 4,606,350 | 8/1986 | Frost . |
| 5,052,388 | 10/1991 | Sivula . |
| 5,127,404 | 7/1992 | Wyborny . |
| 5,137,020 | 8/1992 | Wayne . |
| 5,193,538 | 3/1993 | Ekwall . |

OTHER PUBLICATIONS

"Digital Timing Unit For Programming Biological Stimulators", by Walsh and Moore, Am. J. Med. Electronics 5(1) First Quarter, 1966.

Primary Examiner—George Manuel
Attorney, Agent, or Firm—Reed A. Duthler; Harold R. Patton

[57] ABSTRACT

A pacemaker having a fault-tolerant elective replacement indicator (ERI) triggering scheme in which transient excursions of parameters used as criteria for triggering ERI are rejected as triggering events. Periodic assessments of certain indicia of battery depletion are made, and subjected to a long-term low-pass filtering operation in order to reduce the effects of transient excursions of the indicia which result from non-ERI conditions. Over a long period of time (e.g., a day) predetermined threshold values of the indicia of interest must be exceeded a predetermined number of times in order for the device to issue an ERI. In one disclosed embodiment of the invention, the battery's loaded terminal voltage and internal impedance are used as indicators of the battery's depletion level. Periodically, these values are measured and converted to digital values. The digital values are subjected to a low-pass filtering operation to prevent temporary or transient excursions of the impedance and voltage curves from causing ERI to be triggered. In another disclosed embodiment of the invention, a long term fading average of periodically measured values is maintained. When the measured values are found to fulfill the ERI criteria, assessment of the parameters of interest is performed at an increased rate. While assessments are performed at the increased rate, the continuously updated fading average value must fulfill the ERI triggering criteria at least a predetermined number of times before ERI is triggered. If the fading average fails to fulfill the ERI triggering criteria the required number of times, assessments are resumed at the first, slower periodic rate.

13 Claims, 3 Drawing Sheets

FAULT-TOLERANT ELECTIVE REPLACEMENT INDICATION FOR IMPLANTABLE MEDICAL DEVICE

This is a division of Ser. No. 081,746, filed Jun. 22, 1993.

FIELD OF THE INVENTION

This invention relates to the field of implantable medical devices, and more particularly relates to battery-powered implantable devices having circuitry for monitoring the level of battery depletion.

BACKGROUND OF THE INVENTION

Since the introduction of the first implantable pacemakers in the early 1960s, there have been considerable advancements both in the field of electronics and in the field of medicine, such that there is presently a wide assortment of commercially-available implantable medical devices. The class of implantable medical devices now includes not only pacemakers, but also implantable cardioverters, defibrillators, neural stimulators, and the like. Today's state-of-the-art implantable medical devices are vastly more sophisticated and complex than early pacemakers, and are capable of performing significantly more complex functions. The therapeutic benefits of implantable medical devices have been well proven.

An early pacemaker was disclosed in U.S. Pat. No. 3,057,356 issued to Greatbatch in 1962 and entitled "Medical Cardiac Pacemaker". The Greatbatch pacemaker included a relaxation oscillator for controlling the pacemaker to generate electrical cardiac stimulating pulses. Thus, the pacemaker operated asynchronously to provide fixed-rate cardiac stimulation not automatically changed in accordance with the patient's needs. The Greatbatch pacemaker proved to be effective in alleviating the symptoms of complete heart block. As an asynchronous device, however, the Greatbatch pacemaker had the possible disadvantage of operating to compete with the natural, physiological functioning of the heart during episodes of normal sinus condition.

Since 1962, implantable pulse-generating medical devices have been continuously evolving. For example, in order to overcome the possible disadvantages with asynchronous pacemakers, implantable pacemakers of the synchronous or demand type were developed wherein stimulating pulses are delivered only when required, and are not delivered when the heart functions with a normal sinus rhythm. An early demand-type pacemaker is disclosed, for example, in U.S. Pat. No. 3,478,746 entitled "Cardiac Implantable Demand Pacemaker". The demand pacemaker solves the problem arising with asynchronous pacemakers by inhibiting delivery of stimulating pulses in the presence of detected ventricular activity, and by delivering stimulating pulses only in the absence of natural cardiac activity.

Another improvement which occurred since the first implantable cardiac pacemaker is the ability to reprogram certain operational parameters of the pacemaker after it has been implanted. For example, in U.S. Pat. No. 3,805,796 issued to Terry, Jr. et al. in 1974 and entitled "Implantable Cardiac Pacemaker Having Adjustable Operating Parameters". The Terry, Jr. device included circuitry to allow the rate of the pacemaker to be noninvasively changed after the device was implanted. The stimulation rate was varied according to the number of times that a magnetically actuated reed switch was closed. The device operated to count the number of times the reed switch was closed and storing that count in a binary counter. Each state of the counter was connected to either engage or bypass one resistor in a serially-connected resistor chain, where the resistor chain formed part of the RC time constant controlling pacemaker rate.

The concept of the Terry, Jr. patent has also been improved upon, as exemplified in U.S. Pat. No. 4,066,086 to Adams et al. entitled "Programmable Body Stimulator". The Adams et al. patent discloses a pacemaker that responds to the application of radio frequency (RF) bursts while a magnetic field held in close proximity to a reed switch in the device holds the reed switch closed. In the Adams et al. circuit, only the rate is programmable in response to the number of RF bursts applied. The use of RF signals to program cardiac pacemakers was earlier disclosed in U.S. Pat. No. 3,833,005 issued to Wingrove in 1974 and entitled "Compared Count Digitally Controlled Pacemaker". The Wingrove device was capable of having both pacing rate and pacing pulse width programmed.

Perhaps the most significant advance in implantable device technology, however, has been the incorporation of digital circuitry in implantable devices. Implantable device technology initially lagged behind conventional state-of-the-art electronic technology in its utilization of digital circuits. A primary reason for the delay was that early digital circuits consumed unacceptably large amounts of energy to be used in battery-powered implantable devices impractical. Of course, conservation of battery power in implantable devices has always been a major concern in pacemaker design. Thus, although there were suggestions in the art to utilize digital techniques in cardiac pacemakers even as early as 1966 (see, e.g., Walsh et al., "Digital Timing Unit for Programming Biological Stimulators", *American Journal of Medical Electronics*, First Quarter, 1977, pp. 29-34), one of the first patents suggesting digital techniques in the context of cardiac pacemakers was U.S. Pat. No. 3,557,796 issued to Keller, Jr., et al. in 1971 and entitled "Digital Counter Driven Pacer".

The Keller, Jr. pacemaker included an oscillator driving a binary counter. When the counter reached a certain value, a signal was provided which caused a cardiac stimulating pulse to be provided. At the same time, the counter was reset and began counting oscillator pulses. The Keller, Jr. pacemaker also incorporated a demand feature, and wherein the counter was reset upon detection of a natural heartbeat, as well as a refractory feature, wherein output pulses were inhibited for a certain time after the provision of a cardiac stimulating pulse or natural beat.

Improvements in digital technology and in battery technology have been such that the use of digital circuitry in implantable devices has, over the years, become increasingly feasible and increasingly common. Patents disclosing digital techniques useful in cardiac pacemakers include U.S. Pat. No. 3,631,860 to Lopin entitled "Variable Rate Pacemaker"; U.S. Pat. No. 3,857,399 to Zacouto entitled "Heart Pacer"; U.S. Pat. No. 3,865,119 to Svensson et al. entitled "Heartbeat Accentuated with Controlled Pulse Amplitude"; U.S. Pat. No. 3,870,050 to Greatbatch entitled "Demand Pacer"; U.S. Pat. No. 4,038,991 to Walters entitled "Cardiac Pacer with Rate Limiting Means"; U.S. Pat.

No. 4,043,347 to Renirie entitled "Multiple-Function Demand Pacer with Low Current Drain"; U.S. Pat. No. 4,049,003 to Walters et al. entitled "Digital Cardiac Pacer"; and U.S. Pat. No. 4,049,004 to Walters entitled "Implantable Digital Cardiac Pacer Having Externally Selectable Operating Parameters and One-Shot Digital Pulse Generator for Use Therein".

Examples of what are believed presently to be state-of-the-art pacemakers incorporating digital circuitry are also shown in U.S. Pat. No. 4,250,883 issued to David L. Thompson and entitled "Digital Cardiac Pacemaker"; and in U.S. Pat. No. 5,052,388 to Sivula et al. entitled "Method and Apparatus for Implementing Activity Sensing in a Pulse Generator". The Thompson '883 and Sivula et al. '388 patents are hereby incorporated by reference herein in their respective entireties.

The accuracy and reliability of digital circuits are factors that have encouraged their use in implantable devices. Their ability to be programmed and reprogrammed to alter one or more operating parameters further enhances their utility. For example, the pacemaker disclosed in the above-referenced Sivula et al. patent responds to radio frequency signals from a microprocessor-based external programming unit to alter numerous operating parameters, including pulse rate, pulse width and/or pulse amplitude, pacing mode, sensing mode and sensitivity, activity/rate response settings, refractory periods, AV-delay settings, and others. In U.S. Pat. No. 4,340,062 to Thompson et al. entitled "Body Stimulator Having Selectable Stimulation Energy Levels", there is disclosed a pacemaker in which the amplitude, duration, and repetition rate of cardiac stimulating pulses is externally controllable. The Thompson '062 patent is hereby incorporated by reference herein in its entirety.

Lithium-iodine batteries are among the most commonly used power sources for modern implantable devices, and much has come to be known about their depletion characteristics. In particular, it is well known in the art that the output voltage from lithium-iodine batteries is relatively linear during early stages of depletion, but drops off rather sharply before end-of-life (EOL). This is due in part to the internal resistance of lithium-iodine batteries, which is relatively linear as a function of energy depletion until near EOL, at which time the resistance curve exhibits a "knee" where internal resistance begins to rise rapidly.

In typical lithium-iodine batteries, the cell cathode consists of molecular iodine weakly bonded to polyvinyl pyridine (P2VP). The initial cathode composition of lithium-iodine batteries is often expressed as the weight ratio of $I_2$ to P2VP. Typical values of this ratio range from 20:1 to 50:1. No electrolyte as such is included in the construction of the cell, but a lithium iodine (LiI) electrolyte layer forms during cell discharge, between the anode and the cathode. The LiI layer presents an effective internal resistance to Li+ions which travel through it. Since the LiI layer grows with the charge drawn from the battery, this component of the battery resistance increases linearly as a function of energy depletion. In the implantable device context, where there is typically a relatively continuous energy depletion, this component of the internal resistance increases continually over time. However, particularly for a demand type pacemaker which at any given time may or may not be called upon to deliver stimulating pulses, the increase in this component is continuous but not necessarily linear with time, due to the fact that current drain is not constant.

Another component of internal resistance in lithium-iodine cells is caused by depletion of iodine in the cathode. The cathode is essentially a charge transfer complex of iodine and P2VP, and during discharge of the cell iodine is extracted from this complex. As noted above, the weight ratio of $I_2$ to P2VP at beginning of life may range from 20:1 to 50:1. During extraction of iodine from the complex, the resistance to this process is low until the point is reached where the $I_2$—to—P2VP ratio is reduced to approximately 8:1, the ratio at which the cathode becomes a single phase and the iodine activity begins to be less than unity. At this point the resistance rises sharply. This gives rise to a non-linear internal resistance component which, for the lithium-iodine cell, is called variously the depletion resistance, depolarizer resistance, the charge-transfer complex resistance, or the pyridine resistance. By whatever names, the combination of the non-linear component with the linear component produces an overall resistance curve with a knee occurring toward EOL, the knee being caused by the reaching of the depletion of available charge carriers from the cathode.

Since it is often extremely critical for patients' well-being that implantable devices do not cease operating, it is common for implantable devices to monitor the level of battery depletion and to provide some indication when the depletion reaches a level at which the battery should be replaced. Pacemakers manufactured by Medtronic, Inc., for example, typically provide, for example via telemetry, an "elective replacement indictor" (ERI) when the battery depletion reaches a level such that replacement will soon be needed. Other circuitry in the implantable device may be responsive to issuance of an ERI. In particular, issuance of ERI may cause certain non-essential circuits to be deactivated, in order to decrease the device's overall power consumption and thereby maximize the ERI-to-EOL interval. For example, internal diagnostic functions and advanced rate-response functions may be discontinued upon issuance of ERI. Additionally, the device may revert to a nominal pacing mode (i.e., relatively low rate, demand mode) upon issuance of ERI.

Pacemakers may also provide a battery end-of-life (EOL) indication when the level battery depletion is such that the device can no longer operate properly. Other pacemakers may provide information about battery depletion levels throughout the device's life, for example, whenever the pacemaker is interrogated by an external programmer. In pacemakers which provide an ERI, it is important that there be sufficient time between triggering of ERI and complete battery depletion (battery EOL), so that the device will continue to operate for at least some minimum amount of time after issuance of an ERI. In this way, the physician will have sufficient time to take appropriate action, e.g., to replace the device before battery EOL. At the same time, it is also important not to trigger ERI too early, since it is desirable that the sudden operational changes associated with ERI not be made until it is actually necessary to do so.

In the prior art, some ERI arrangements in implantable devices evaluate battery life based simply upon the loaded terminal voltage of the battery, indicating ERI or EOL when the voltage falls below a predetermined threshold. For example, in U.S. Pat. No. 4,313,079 to Lee, there is described a battery depletion monitor which employs a CMOS inverter to compare the battery voltage to a reference voltage. When the reference voltage exceeds the measured battery voltage, the inverter changes state to indicate battery depletion. However, due to the internal impedance characteristics of the battery, discussed above, a battery's loaded terminal voltage can vary significantly depending upon current consumption. Thus, if relatively little current is drawn from the battery for a period of time when the battery is nearing but has not reached the ERI point, a sudden prolonged period of high demand on the battery may cause a situation in which too little time is available between ERI and total depletion of the battery. For a particular pacemaker and electrode combination in a given patient, there will be a variation in the effective load on the lithium-iodine battery, and a resulting variation in the overall current drain. Accordingly, if ERI is predicated upon sensing the voltage of the battery and detecting when it drops below a certain level, there can be very little assurance that the level chosen will correspond to the knee of the internal resistance curve.

It has been recognized in the prior art that since remaining battery life is directly related to the internal impedance of the battery itself, remaining battery life can be reliably predicted through accurate measurement of internal battery impedance. Such reliability arises from the fact that battery impedance is nearly independent of current drain.

In U.S. Pat. No. 5,137,020 issued to Wayne et al. and assigned to the assignee of the present invention, there is described a battery impedance measuring arrangement wherein a current source and a reference impedance are applied to a battery which has been isolated from the remainder of the pacemaker circuitry. The Wayne et al. '020 patent is hereby incorporated by reference in its entirety into the present disclosure.

Other battery impedance measuring arrangements are proposed, for example, in U.S. Pat. Nos. 4,259,639 to Renirie, 4,231,027 to Mann et al., and 4,324,251 to Mann. These patents are also hereby incorporated by reference herein in their respective entireties. The theory underlying the use of internal impedance as an EOL warning indicator is that at low current drains typical of implantable medical devices, plots of resistance versus time give more warning than plots of terminal voltage over time. If voltage characteristics for different current drains are considered, the knees in the impedance curve are observed to have a fairly wide variation, meaning that the voltage at which the knee might appear is similarly subject to substantial variation as a function not only of the particular battery being used but also of the current being drawn by the pacemaker circuitry at a given time. On the other hand, plots of resistance indicate that the knee varies over a smaller range of values of internal resistance. Since the current drain may vary drastically with different electrode loads, the variation in voltage may be twice as great as the variation in internal resistance. Monitoring the internal resistance thus provides a somewhat more direct indication of the depth of discharge of the battery, whereas monitoring the output voltage gives a less direct indication, reflecting not only the depth of discharge but also the current drain.

In recognition of the usefulness of battery impedance as a measure of battery depletion, there have been proposed in the prior art various different schemes for using battery impedance as an ERI detection criterion. In U.S. Pat. No. 4,448,197 to Nappholz et al., for example, there is described a pacemaker in which battery depletion is monitored by periodically applying a reference current to the terminals of the pacemaker's battery to measure the battery's internal resistance. The reference current level is programmably selectable from multiple values, so that an appropriate one can be chosen based upon the physician's assessment of the expected nominal current drain of the device when programmed for a particular patient.

In U.S. Pat. No. 4,290,429 to Blaser, there is described still another battery depletion monitoring circuit which takes into account both the battery's terminal voltage and the internal impedance of the battery. The Blaser circuit includes a voltage comparator for monitoring the battery's terminal voltage, and an impedance measuring circuit for applying to the voltage comparator a signal representative of the internal impedance of the battery. If either the internal impedance or the terminal voltage is found to meet specified ERI criteria, an ERI is triggered. However, the Blaser circuit does not appear take into account all of the above-described problems with transients in the demand on the battery (i.e., transients in the current drain in the device).

Generally speaking, there are three primary causes of transient excursions in the current demand curve in an implantable device: periods of aberrantly low current demand, periods of aberrantly high current demand, and exposure to externally generated electromagnetic fields. Periods of aberrantly low current demand may occur, for example, when the patient's intrinsic cardiac activity is such that no stimulating pulses are required for a period of time. Periods of aberrantly high current demand may occur, for example, when the pacemaker is pacing at or near its upper rate, or when the pacemaker is transmitting an uplink telemetry signal.

Given the causes for transient excursions of the demand curve for the battery in an implantable device, there are two principle types of errors that can occur in triggering ERI based upon criteria affected by current demand transients. One type of error arises when a period of aberrantly high current demand is used as the basis for triggering ERI. This error results in ERI possibly being triggered too early.

While measurement of battery impedance has been shown to be useful for rejecting current transients as ERI criteria, another problem with using impedance as an ERI criterion is that the ERI-to-EOL interval is roughly inversely proportional to the average current drain on the battery. That is, since battery impedance is nearly independent of current drain, when a given ERI impedance threshold is reached there will be a given level of remaining battery capacity regardless of the current drain. For high current drain, this remaining capacity is consumed more quickly than for low current drain. Thus, a high current drain must be assumed in selecting an ERI impedance threshold, in order to ensure a reasonable ERI-to-EOL interval in all cases. This can lead to wasted battery capacity in cases where current drain is, in fact, low.

On the other hand, when the battery's voltage is used as an ERI criterion, the remaining capacity when a given ERI threshold voltage is reached is greater when current demand is consistently high than when it is consistently low. However, the battery voltage is susceptible to the above-noted problems associated with transients in the current demand. Thus, the advantages of using battery voltage as an ERI criterion are seen only if voltage fluctuations due to current transients can be rejected.

It is believed that none of the ERI triggering schemes in the prior art completely addresses the all of the above-described types of problems with current transients and with early ERI triggering in cases of consistently high current demand.

SUMMARY OF THE INVENTION

The present invention, therefore, relates to a pacemaker or other human-implantable device which employs an ERI detection scheme believed to be more "fault-tolerant" than those of the prior art. In particular, the present invention relates to a pacemaker in which the above-described various types of transient excursions of the battery's demand curve are rejected as criteria for triggering ERI. At the same time, the present invention relates to a pacemaker in which early ERI triggering is avoided.

In accordance with one aspect of the present invention, circuitry is provided in the implantable device for periodically assessing the depth of discharge of the device's battery. In accordance with another aspect of the present invention, one or more indicia of battery discharge may be assessed, for example, the battery's open-circuit terminal voltage, the battery's internal resistance, the battery's geometric capacitance, and/or other conditions which reflect the depletion level of the battery.

In order to take into account the perceived problems in the prior art of avoiding triggering ERI based upon transient excursions of the indicator(s) used to assess battery depletion, the ERI circuitry in accordance with one aspect of the present invention performs a filtering function upon a plurality of measurements of the indictor(s) of interest. In this way, temporary spurious excursions of the indicator to levels which could otherwise reflect a depletion condition are rejected as criteria for triggering ERI.

In one disclosed embodiment of the invention, circuitry is provided for periodically assessing both the loaded terminal voltage and the internal impedance of the battery. The measured voltage is compared with a predetermined (minimum) threshold voltage value, and a first ERI triggering criteria is deemed fulfilled if the measured voltage is lower than the predetermined threshold voltage. The measured internal impedance of the battery is compared with a predetermined (maximum) impedance threshold, and a second ERI triggering criteria is deemed fulfilled if the measured value is greater than the predetermined maximum impedance threshold.

If both the first and second criteria are fulfilled, the value in an ERI status register is incremented by a known value. The assessment of the voltage and impedance value is repeated every three hours during every twenty-four hour period. If the value in the ERI status register exceeds a predetermined maximum level within a twenty-four hour period, an ERI is issued. Otherwise, the ERI status register is reset to a zero value at the beginning of each twenty-four hour period and the three-hour assessments are resumed.

In another disclosed embodiment of the invention, circuitry is provided for assessing ERI criteria each time a first predetermined time interval elapses. After each assessment, the new measured value is incorporated into a long-term running average of previously measured values. If the assessment of the criteria indicates that the battery has possibly depleted to an ERI condition, the periodic assessments are conducted with increased frequency, i.e., each time a second predetermined time interval, shorter than the first, elapses. The running average is also updated at this increased rate. If the ERI triggering criteria are satisfied by the running average value a predetermined number of times that the assessment is made at the increased rate, ERI is triggered. If, while assessments are performed at the increased rate, the running average does not satisfy the ERI triggering criteria a predetermined number of times, the assessments are resumed at the first, slower rate.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF SPECIFIC EMBODIMENTS OF THE INVENTION

Figure 1:
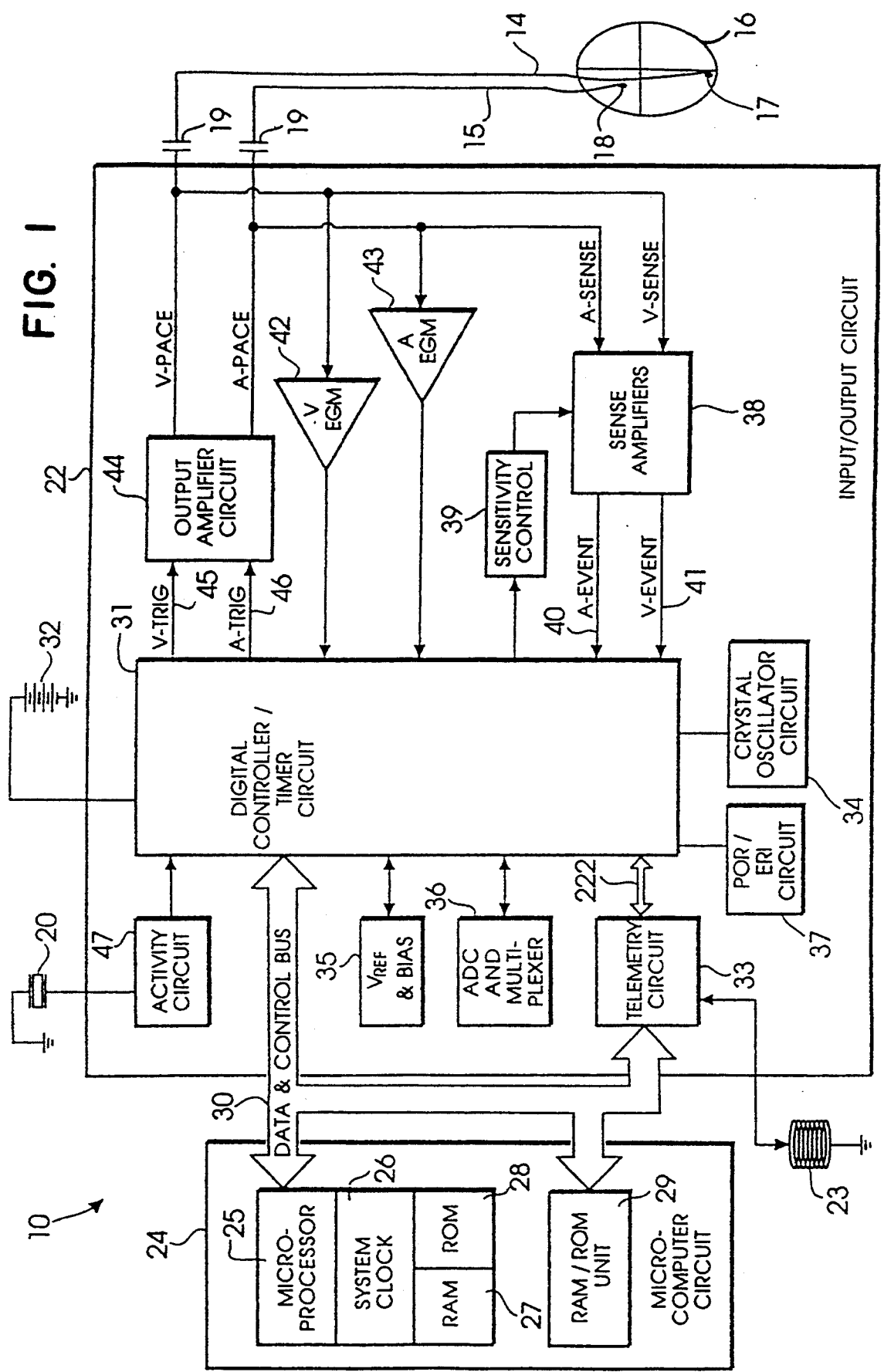
FIG. 1 is a block diagram of an implantable pacemaker in accordance with one embodiment of the invention.

Referring to FIG. 1, there is shown a block diagram of an implantable pacemaker 10 which incorporates a telemetry subsystem in accordance with the present invention. Although the present invention will be described herein in conjunction with a pacemaker 10 having a microprocessor-based architecture, it will be understood that pacemaker 10 may be implemented in any logic based, custom integrated circuit architecture, if desired. The pacemaker shown in FIG. 1 is substantially similar to that disclosed in co-pending U.S. patent application Ser. No. 07/794,766 filed by Paul Stein and entitled "Method and Apparatus for Implementing Activity Sensing in a Pulse Generator", and in co-pending U.S. patent application Ser. No. 07/870,062 filed by Wahlstrand et al. entitled "Method and Apparatus for Rate-Responsive Cardiac Pacing". The Stein 07/794,766 and Wahlstrand 07/870,062 applications are each hereby incorporated herein by reference in their entireties.

Although a particular implementation of a pacemaker is disclosed herein, it is to be understood that the present invention may be advantageously practiced in conjunction with many different types of pacemakers, such as the pacemaker described in the above-referenced Sivula et al. patent, for example, as well as other types of implantable medical devices.

In FIG. 1, pacemaker 10 is shown to include an activity sensor 20, which may be, for example, a piezoelectric element bonded to the inside of the pacemaker's shield. Such a pacemaker/activity sensor configuration is the subject of the above-referenced patent to Anderson et al. Piezoelectric sensor 20 provides a sensor output which varies as a function of a measured parameter that relates to the metabolic requirements of a patient.

Pacemaker 10 of FIG. 1 is programmable by means of an external programming unit (not shown in FIG. 1). One such programmer suitable for the purposes of the present invention is the Medtronic Model 9760 programmer which is commercially available and is intended to be used with all Medtronic pacemakers. The 9760 programmer is a microprocessor-based device which provides a series of encoded signals to pacemaker 10 by means of a programming head which transmits radio-frequency (RF) encoded signals to pacemaker 10 according to the telemetry system laid out, for example, in U.S. Pat. No. 5,127,404 to Wyborny et al. entitled "Improved Telemetry Format", which is assigned to the assignee of the present invention and which is incorporated herein by reference in its entirety. It is to be understood, however, that the programming methodology disclosed in the above-referenced patent is identified herein for the purposes of illustration only, and that any programming methodology may be employed so long as the desired information can be conveyed between the pacemaker and the external programmer.

It is believed that one of skill in the art would be able to choose from any of a number of available pacemaker programmers and programming techniques to accomplish the tasks necessary for practicing the present invention. As noted above, however, the Medtronic Model 9760 programmer is presently preferred by the inventors.

In the illustrative embodiment of the present invention, parameters such as the lower rate of pacemaker 10 may be programmable, for example from 40 to 90 pulses per minute (PPM) in increments of 10 PPM, and the upper rate may be programmable, for example, between 100 and 175 PPM in 25 PPM increments. There may also be programmable rate response functions in pacemaker 10. In addition, pacemaker 10 has, in accordance with one embodiment of the present invention, a plurality of programmable output pulse energy settings. In particular, the output pulse energy level is programmable from 0 to 7.5-V in 0.5-V increments.

Pacemaker 10 is schematically shown in FIG. 1 to be electrically coupled via pacing lead 14 and 15 to a patient's heart 16. Leads 14 and 15 include one or more intracardiac electrodes, depending upon whether they are unipolar or bipolar leads. As would be appreciated by those of ordinary skill in the art, bipolar leads include separate, electrically isolated tip and ring electrodes, while unipolar leads include a single tip electrode. For the sake of illustration, electrodes designated as 17 and 18 are shown in FIG. 1, located near their distal ends of leads 14 and 15, respectively, and positioned within the right ventricular (RV) and right atrial (RA) chambers, respectively, of heart 16. It is to be understood, however, that leads 14 and 15 may be of either the unipolar or bipolar type as is well known in the art.

Electrodes 17 and 18 are coupled via suitable lead conductors through input/output terminals of an input/output circuit 22. In the presently disclosed embodiment, activity sensor 20 is bonded to the inside of the pacemaker's outer protective shield, in accordance with common practice in the art. As shown in FIG. 1, the output from activity sensor 20 is also coupled to input/output circuit 22.

Input/output circuit 22 contains the analog circuits for interface to the heart 16, activity sensor 20, and antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 1 is powered by an appropriate implantable battery power source 32, in accordance with common practice in the art. In the presently disclosed embodiment of the invention, power source 32 is a lithium-iodine battery. Lithium-iodine batteries suitable for the purposes of the present invention are well-known and commercially-available from a number of manufacturers. For the sake of clarity, the coupling of battery power to the various components of pacemaker 10 has not been shown in the Figures.

An antenna 23 is connected to input/output circuit 22 for purposes of uplink/downlink telemetry through an RF telemetry circuit 33 in accordance with one embodiment of the invention, to be hereinafter described in greater detail. In the embodiment of FIG. 1, telemetry circuit 33 is coupled to digital controller/timer circuit 31. It is contemplated that telemetry circuit 33 may also be coupled directly to microcomputer circuit 24 via data and control bus 30.

A crystal oscillator circuit 34, typically a 32,768-Hz crystal-controlled oscillator, provides main timing clock signals to digital controller/timer circuit 31. A $V_{REF}$ and Bias circuit 35 generates stable voltage reference and bias currents for the analog circuits of input/output circuit 22. An analog-to-digital converter (ADC) and multiplexer unit 36 digitizes analog signals and voltages to provide "real-time" telemetry intracardiac signals and battery elective replacement indicator (ERI) and end-of-life (EOL) functions.

A power-on-reset and elective replacement indicator (POR/ERI) circuit 37 functions as a means to reset circuitry and related functions to a default condition upon detection of a low battery condition, which will occur upon initial device power-up or will transiently occur in the presence of electromagnetic interference, for example. POR/ERI circuit 37 also functions to monitor the depth of discharge of battery 32, as will be hereinafter described in greater detail, and informs digital controller/timer circuit 31 when an ERI should be issued.

In particular, POR/ERI circuit 37 in accordance with the presently disclosed embodiment of the invention issues an ERI when certain criteria relating to the battery's output voltage and internal impedance are fulfilled, as will be hereinafter described in greater detail.

The operating commands for controlling the timing of pacemaker 10 are coupled by bus 30 to digital controller/timer circuit 31 wherein digital timers, registers, and counters are employed to establish the overall escape interval of the pacemaker, as well as various refractory, blanking, and other timing windows for controlling the operation of the peripheral components within input/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to a conductor in lead 14 to receive a V-SENSE signal from heart 16. Similarly, an A-EGM (atrial electrocardiogram) amplifier 43 is coupled to one conductor of lead 15 to receive the A-SENSE signal from heart 16. The electrogram signals developed by V-EGM amplifier 42 and A-EGM amplifier 43 are used on those occasions when the implanted device is being interrogated by external programmer 11, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference.

Digital controller and timer circuit 31 is coupled to an output amplifier circuit 44 via two lines 45 and 46, designated V-TRIG (ventricular trigger) and A-TRIG (atrial trigger), respectively. Circuit 31 asserts the V-TRIG signal on line 45 in order to initiate the delivery of a ventricular stimulating pulse to heart 16 via pace/sense lead 14. Likewise, circuit 31 asserts the A-TRIG signal on line 46 to initiate delivery of an atrial stimulating pulse to heart 16 via pace/sense lead 15. Output amplifier circuit 44 provides a ventricular pacing pulse (V-PACE) to the right ventricle of heart 16 in response to the V-TRIG signal developed by digital controller/timer circuit 31 each time the ventricular escape interval times out, or an externally transmitted pacing command has been received, or in response to other stored commands as is well known in the pacing art. Similarly, output amplifier circuit 44 provides an atrial pacing pulse (A-PACE) to the right atrium of heart 16 in response to the A-TRIG signal developed by digital controller/timer circuit 31. Output amplifier circuit 44 includes one or more output amplifiers which may correspond generally to that disclosed in U.S. Pat. No. 4,476,868 issued to Thompson on Oct. 16, 1984 also incorporated herein by reference in its entirety.

As would be appreciated by those of ordinary skill in the art, input/output circuitry will include decoupling circuitry for temporarily decoupling sense amplifier circuit 38, V-EGM amplifier 42 and A-EGM amplifier 43 from leads 14 and 15 when stimulating pulses are being delivered from output control circuit 48. For the sake of clarity, such decoupling circuitry is not depicted in FIG. 2.

While specific embodiments of sense amplifier circuitry and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. application. It is believed that the particular implementation of activity circuit 47 is not critical to an understanding of the present invention, and that various activity circuits are well-known to those of ordinary skill in the pacing art.

As previously noted, digital controller/timer circuit 31 includes certain registers for storing digital data used in the control of pacemaker functions. In the case of programmable functions, the digital data representing selected values for programmable parameters may be downloaded from an external programming device to pacemaker 10 via the telemetry link. As would be appreciated by those of ordinary skill in the art, a downloaded digital value can contain bits identifying the parameter to be programmed and bits identifying the selected value for that parameter.

One of the registers maintained in digital controller/timer circuit 31 is an eight-bit register called the ERI status register. As will be hereinafter described in greater detail, digital controller/timer circuit 31 accumulates information about the level of battery depletion over a twenty-four hour period and triggers an ERI when sufficiently low remaining battery capacity is detected. Every twenty-four hours the ERI status register is reset.

POR/ERI circuit 37 includes circuitry for performing measurements to determine the depletion level of battery 32. In particular, ERI circuit 37 includes a battery impedance measurement circuit for determining the battery's internal impedance, as well as a battery voltage measurement circuit for determining the battery's loaded terminal voltage. The impedance measurement circuit may be of the type disclosed in the above-referenced Wayne et al. '020 patent or in the above-referenced Renirie '639 patent. It is believed by the inventors that for the purposes of practicing the present invention, those of ordinary skill in the art would be able to select a suitable depletion monitoring circuit from among the various known circuits in the prior art. It is further believed that the details of implementation of particular depletion monitoring circuitry in POR/ERI circuit 37 are not necessary for an understanding of the present invention, and that those of ordinary skill in the art having the benefit of the present disclosure will be readily able to practice the present invention.

In the presently disclosed embodiment of the invention, POR/ERI circuit 37 defines separate battery impedance and voltage criteria which must be fulfilled before an ERI is issued. In particular, ERI circuit 37 periodically measures the battery's output voltage. In the presently preferred embodiment of the invention, the battery's voltage is measured just prior to delivery of a pacing pulse, so that the battery is allowed to recover from any momentary excursion of the output voltage due to delivery of a pacing pulse.

If the measured battery voltage is found to be below a predetermined ERI voltage threshold, POR/ERI circuit 37 then measures the battery's internal impedance. If the battery impedance is greater than a predetermined ERI impedance threshold, circuit 37 will cause the current value stored in the ERI status register to be incremented by sixty-four. Digital controller/timer circuit 31 and microcomputer circuit 24 cooperate such that if the value in the ERI status register exceeds 255, an ERI is triggered, causing pacemaker 10 to enter an ERI mode to minimize power consumption. In the ERI mode, various power-consuming features of pacemaker 10 may be disabled, so that the period between ERI and EOL can be maximized.

Figure 2:
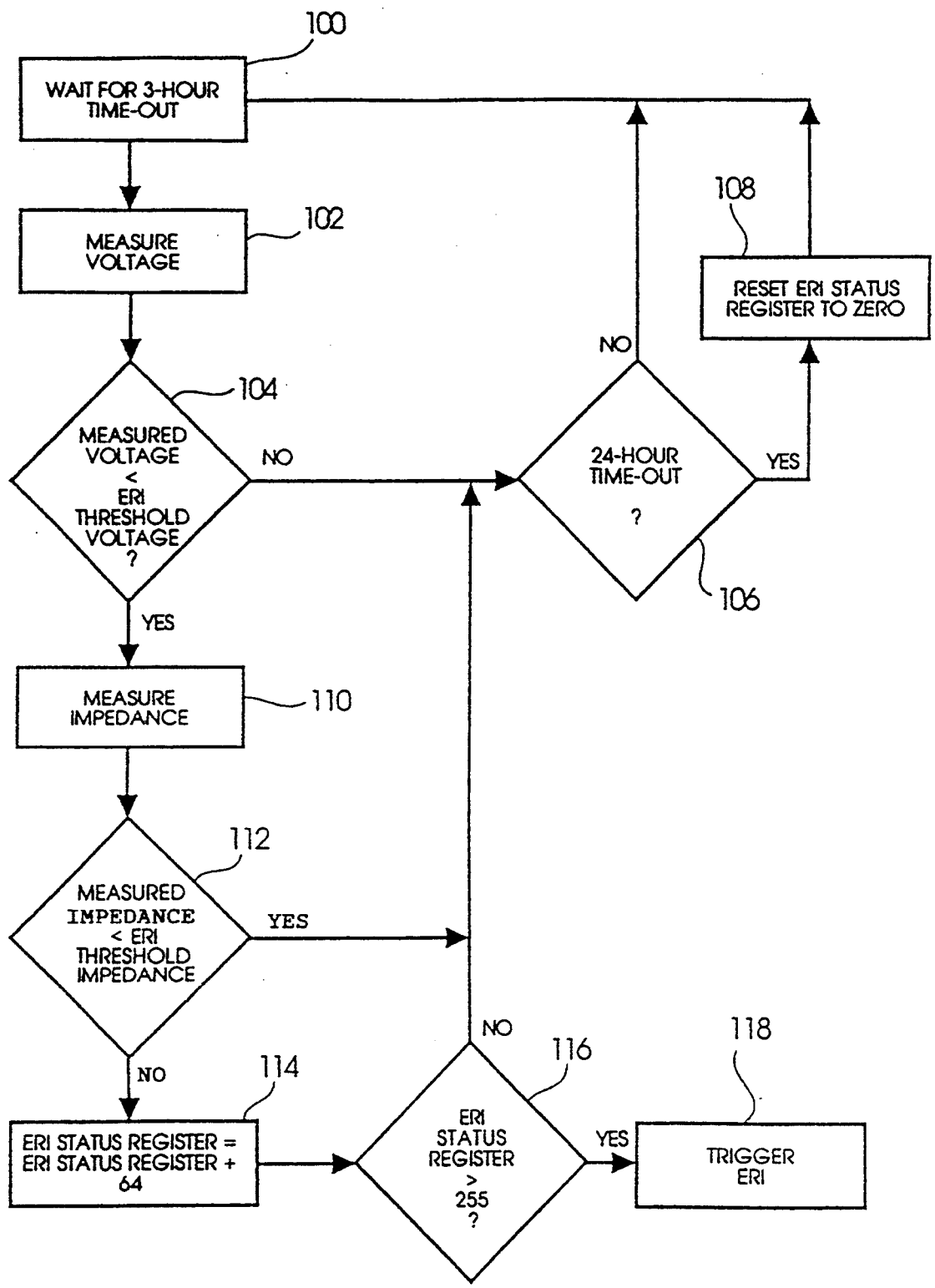
FIG. 2 is a flow diagram illustrating the steps performed by the pacemaker from FIG. 1 in determining when to trigger ERI in accordance with one embodiment of the invention.

The averaging function performed by pacemaker 10 upon the criteria (voltage and impedance) used for triggering ERI will perhaps be best understood with reference to the flow diagram of FIG. 2. In particular, FIG. 2 illustrates the steps performed by digital controller/timer circuit 31 in cooperation with microcomputer circuit 24 in determining when to trigger ERI. The process begins, in FIG. 2, at the block designated 100, in which pacemaker 10 is waiting for a three-hour time interval to elapse between ERI cycles. It is contemplated that this three-hour time interval may be measured using one of the aforementioned timers included in digital controller/timer circuit 31, as would be appreciated by those of ordinary skill in the art.

When a three-hour time-out occurs in block 100, the next step, represented by block 102 in FIG. 2, is to measure the loaded terminal voltage of battery 32. In particular, digital controller/timer circuit 31 issues a control signal to POR/ERI circuit 37 to cause circuit 37 to measure the loaded terminal voltage of battery 32. This measurement step may be performed in accordance with the teachings of the above-referenced Lee '079 patent, for example, although it is believed that other voltage measurement circuits in the prior art would be equally suitable for the purposes of practicing the present invention.

From block 102, flow proceeds to block 104, wherein the measured battery voltage obtained in block 102 is compared to a predetermined ERI threshold voltage. In the presently disclosed embodiment of the invention, battery 32 is a lithium-iodine battery, commercially available from Promeon Corp., Minneapolis, Minn., having an open circuit voltage of approximately 2.8-V at beginning of life (BOL). For such a battery, an appropriate ERI threshold voltage will typically be on the order of 2.2- to 2.68-V or so, although it is contemplated that the selection of an ERI threshold voltage may involve consideration of other implementation-specific factors, such as the desired ERI-to-EOL interval, the desired device longevity, and so on. As would be appreciated by those of ordinary skill in the art, a higher ERI threshold voltage will cause the voltage criterion for ERI triggering to be fulfilled at an earlier point than a lower one. Thus, depending upon the desired interval between ERI and EOL, a different ERI threshold voltage may be selected. As will be appreciated by those of ordinary skill in the art, the ERI threshold voltage may be a programmable parameter that may be specified by a physician using an external programmer, or may be a preset, non-programmable value.

It is contemplated by the inventors that the comparison of the measured battery voltage to an ERI threshold voltage performed in block 104 in FIG. 2 may involve the conversion, in ADC 36 (see FIG. 1) of the measured voltage to a digital value. The digital representation of the measured voltage may then be compared to a digital threshold value. Alternatively, the comparison of block 104 may be performed using a conventional analog comparator circuit contained in POR/ERI circuit 37.

If the comparison in block 104 indicates that the measured voltage is greater than or equal to the ERI threshold voltage, the operation of digital controller/timer circuit 31 and microcomputer circuit 24 branches to block 106, where a determination is made whether a 24-hour time interval has elapsed since the ERI status register was last reset to zero. If not, operation returns to block 100 where pacemaker 10 waits for another three-hour time out. If twenty-four hours has elapsed, however, the ERI status register is reset to zero, in block 108, prior to returning to block 100.

If the comparison in block 104 indicates that the measured voltage is less than the ERI threshold voltage, however, the operation proceeds to block 110, wherein the internal impedance of battery 32 is measured. The impedance measurement may be performed by POR/ERI circuit in accordance with the teachings of the above-referenced Wayne et al. '020 or Renirie '639 patents, for example, although it is believed that other prior art impedance measurement schemes may be equally suitable for the purposes of practicing the present invention.

After the battery impedance has been measured in block 110, the measured impedance value is compared to predetermined ERI threshold impedance value, in block 112. Again, it is contemplated that the ERI threshold impedance value may be a programmable parameter or may be a preset, non-programmable one. Providing programmable ERI criteria would enable a physician to control, to some extent, the ERI-to-EOL interval for a patient, which may be desirable. As for the comparison in block 104, it is contemplated that the comparison in block 112 may involve conversion of the measured value to a digital value in ADC 36, or may be performed using a conventional analog comparator circuit. In either case, if the measured impedance is found to be less than 112, this indicates that the ERI criteria have not been fulfilled, and the operation proceeds to block 106. As before, in block 106 it is determined whether 24-hours has elapsed since the ERI status register was last reset; if so, the ERI status register is reset before operation returns to block 100, to wait for another three-hour time-out.

On the other hand, if the comparison in block 112 indicates that the battery's internal impedance exceeds the ERI threshold impedance value, this represents the fulfillment of the second ERI triggering condition. Therefore, the ERI status register value is incremented by 64, as indicated by block 114 in FIG. 2. Next, in block 116, it is determined whether the ERI status register value is greater than 255. Only when the ERI value is greater than 255 is ERI triggered, as represented by block 118. If the ERI value is less than or equal to 255, operation branches to block 106 to check for a 24-hour time-out, as previously described.

It is contemplated by the inventors that in addition to voltage and impedance, there may be other parameters which could be monitored in the determination of when to trigger ERI. For example, in co-pending U.S. patent application Ser. No. 08/053,108, entitled "Measurement of Depth-of-Discharge of Lithium Batteries" filed in the name of Craig Schmidt et al. and commonly assigned to the assignee of the present invention, there is described a battery depletion monitoring circuit which, in addition to measuring voltage and impedance further measures the geometric capacitance of the battery in order to assess the level of depletion of the battery. The Schmidt et al. application is hereby incorporated by reference herein in its entirety.

If it is desired to establish additional criteria, such as geometric capacitance, for the determination of when to trigger ERI, it is contemplated that after the comparison operation in block 112 of FIG. 2 is performed and it is determined that the measured impedance is greater than the ERI threshold impedance value, such additional criteria would then be evaluated before the ERI status register value is incremented. In particular, as many criteria as desired could be established, and microcomputer circuit 24 and digital controller/timer circuit 31 would cooperate to increment the ERI status register value only upon fulfillment of each of the established criteria.

It is further contemplated that the fulfillment of different criteria may result in different values being added to the ERI status register value. That is, the importance of each criterion could be "weighted", for example, according to the degree of correlation between the parameter being monitored and the actual depletion level of the battery. For example, output amplifier circuit 44 may incorporate charge monitoring circuitry for ensuring that the pacemaker's output capacitors are fully charged each time a pacing pulse is delivered. If the monitoring circuitry determined that the output capacitors in output circuit 44 are not being fully charged, it may provide some indication of "low supply" to digital controller/timer circuit 31. Controller circuit 31, in response to this low supply indication, could then operate to add some value, greater or less than 64, to the ERI status register, reflecting the possibility that the failure of the output capacitors to be fully charge is due to depletion of the battery.

It is believed that those of ordinary skill in the art having the benefit of the present disclosure would be readily able to incorporate additional ERI criteria into the presently disclosed embodiment of the invention.

As will be appreciated by those of ordinary skill in the art, the above-described cooperation of microcomputer circuit 24 and digital controller/timer circuit 31 effectively results in a digital low-pass filtering of the criteria used in the determination of when to trigger ERI. This low-pass filtering operation enables pacemaker 10 to reject, as ERI triggering criteria, the above-described transient excursions in the various values monitored.

Figure 3:
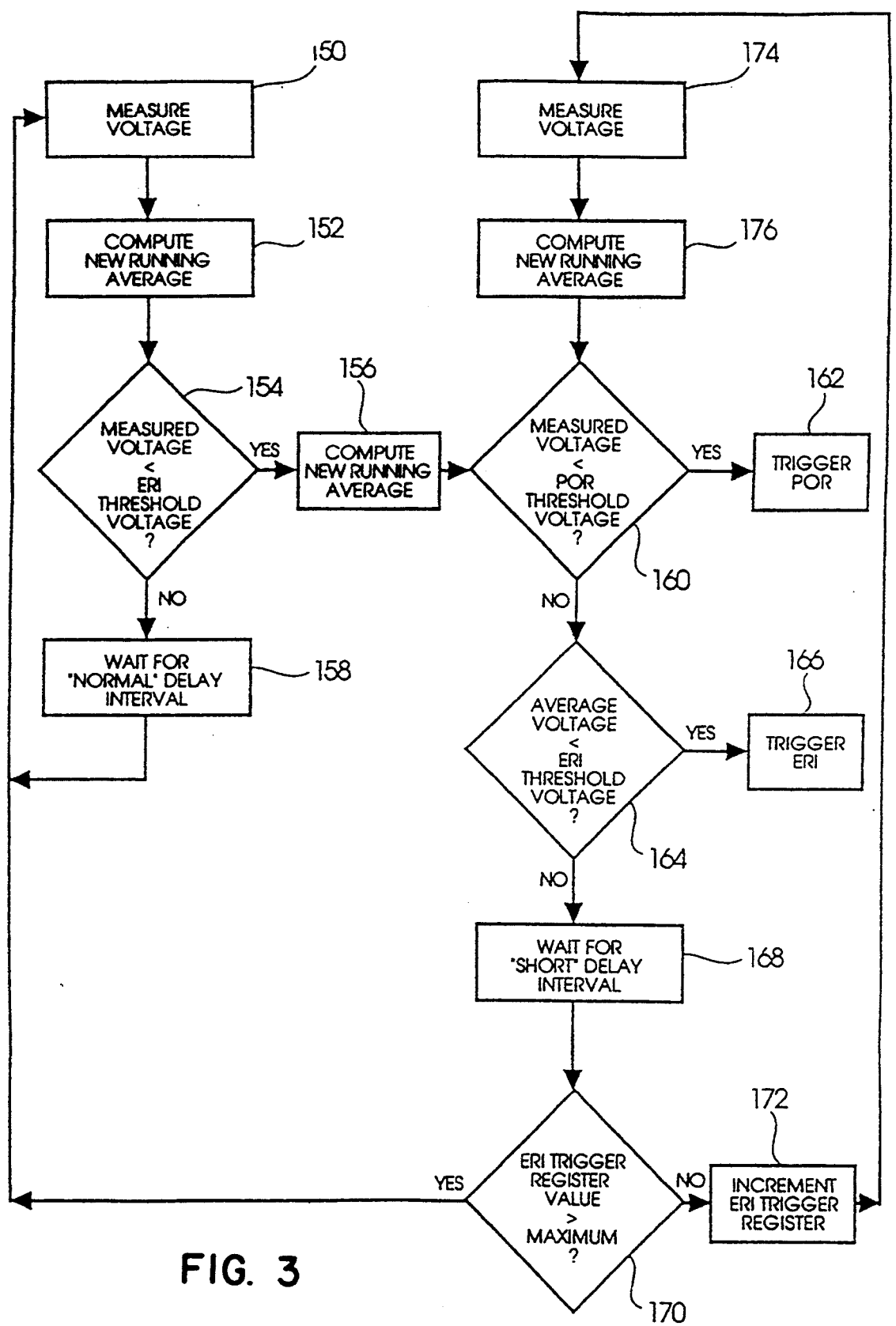
FIG. 3 is a flow diagram illustrating the steps performed by the pacemaker of FIG. 1 in determining when to trigger ERI in accordance with another embodiment of the invention.

Turning now to FIG. 3, there is shown a flow diagram for an alternative implementation of the present invention, which involves a so-called "fading average" of values used as ERI criteria. The embodiment of FIG. 3 will be described herein in terms of only a single ERI triggering criterion, namely the decrease in battery voltage below the ERI threshold voltage. However, it is believed that those of ordinary skill in the art having the benefit of the present disclosure would be readily able to include additional ERI triggering criteria into the embodiment of FIG. 3.

The operations illustrated in FIG. 3 begin in block 150 with measurement of the ERI criterion value, which in the presently disclosed embodiment of the invention is the loaded terminal voltage of battery 32. Next, in block 152, microcomputer circuit 24 performs a running averaging function with the measured value and previously measured values, and stores the resulting running average in a register. One averaging function that is believed to be suitable for the purposes of the present invention is an infinite impulse response time averaging function of the form $$y(n) = Ay(n-1) + Bx(n)$$

where $y(n-1)$ is the previous running average value, $x(n)$ is the new measured value, $y(n)$ is the new running average value, and $A+B=1$ to provide the desired low-pass response. In particular, it is believed that values of $A=0.9375$ and $B=0.0625$ are suitable, where $Ay(n-1)$ can be efficiently implemented by microcomputer circuit 24 as follows:

$Bx(n)$ may be efficiently computed as $x(n)$ over 16.

$$Ay(n-1) = \frac{y(n-1)}{2} + \frac{y(n-1)}{4} + \frac{y(n-1)}{8} + \frac{y(n-1)}{16}$$

With continued reference to FIG. 3, after the above-described averaging function is performed in block 152, a determination is made in block 154 whether the measured value is less than a predetermined ERI threshold value. If so, in block 156 an ERI triggering counter is reset to zero. However, in block 154 if the measured value is found to exceed the ERI threshold, flow proceeds to block 158, where pacemaker 10 waits for a "normal" delay interval to elapse. In the presently disclosed embodiment of the invention the "normal" delay of block 158 is selected to ensure that the ERI criterion is evaluated frequently enough to ensure a sufficient ERI-to-EOL interval. In particular, it has been experimentally shown that for a typical 90-day ERI-to-EOL interval, the voltage of battery 32 can decline by approximately 540-mV or so, which amounts to 6.00-mV per day over the ERI-to-EOL interval. Assuming an approximate 3-mV measurement precision in POR/ERI circuit 37, sampling the battery voltage every twelve hours is therefore sufficient to detect the 6.00-mV per day changes in battery voltage. In order to provide redundancy, two-times sampling can be employed (i.e., every six hours). To compensate for the fundamental circadian frequency of six hours, the "normal" delay is, in the presently disclosed embodiment of the invention, chosen to be three hours.

Thus, after three hours has elapsed in block 158, operation returns to block 150 to proceed as previously described.

At some point, the battery depletion level will be such that the comparison in block 154 will indicate that the measured value is less than the ERI threshold value, in which case the ERI triggering counter in digital controller/timer circuit 31 is reset to zero. Then, in block 160, the measured value is compared to a POR threshold value to determine whether the battery has reached EOL or otherwise fallen below the minimum level required for proper functioning of the device. If so, POR is initiated to restore all circuitry to nominal power-up conditions, as indicated by block 162.

If POR is not indicated in block 160, operation proceeds to block 164, wherein the running average value computed in block 152 is compared to the ERI threshold value. If the average value is found to be less than the threshold, this is used to trigger ERI, as indicated by block 166. If the average value is not less than the ERI threshold in block 165, operation proceeds to block 168, where pacemaker 10 waits for a "short" delay interval to elapse. In the presently disclosed embodiment of the invention, the "short" delay is selected to be, for example, 30 minutes. After the short delay in block 168, the value in the ERI triggering register is compared to a predetermined maximum value, as indicated by block 170 in FIG. 2. If the ERI triggering register value has not reached the predetermined maximum value, which in the presently disclosed embodiment of the invention may be chosen to be 8 consecutive measures, operation branches to block 172, where the ERI triggering register is incremented. Next, in block 174, the battery voltage is measured again, as in block 150, and in block 176 the new measured value is incorporated into the running average value as previously described for block 152. Then, operation returns to block 160.

If the loop comprising blocks 172, 160, 164, 168, and 170 executes for a predetermined number of times (i.e., the predetermined maximum value for the ERI triggering register, then in block 170 operation will return to block 150. This will occur when the comparison in block 154 indicated that the measured voltage dropped below the ERI threshold value due to a transient condition rather than actual depletion of the battery.

The operation just described with reference to FIG. 3 results in a "fading average" of the measured value used as an ERI criterion. This fading average is believed to be particularly effective in ensuring that the measurement of the battery voltage is made at the right times, i.e., not so infrequently that the ERI-to-EOL interval is too short, and not so frequently that occasional or even periodic transient excursions in the value lead to premature ERI triggering. As described above, this is accomplished by providing for a "normal" interval between measurements, and a "short" interval between measurements which is used when it appears that the measured value has dropped below the ERI threshold. This facilitates rejection of transient excursions as ERI criteria.

It is believed that the fading average function described with reference to FIG. 3 is particularly advantageous for ERI determination, given the fact that battery voltage decays over time. With the function of FIG. 3, measurements are made more frequently as the battery voltage gets nearer to the ERI trip point. Given the battery decay characteristic, a fading average advantageously provides preferential bias to recent measurements as the ERI trip point approaches.

In view of the foregoing detailed description of specific embodiments of the invention, it should be apparent to those of ordinary skill in the art that a pacemaker with a fault-tolerant ERI scheme has been disclosed. Although specific embodiments of the invention have been described in detail, and although the invention has been described herein in the context of an implantable pacemaker, this has been done for the purposes of illustrating the present invention only, and is not intended to be limiting with regard to the scope of the invention. In particular, the present invention is not believed to be limited to utilization in pacemakers, and it is believed that the present invention may be advantageously practiced in conjunction with many types of battery-powered devices. In addition, although the disclosed embodiments have referred to battery voltage and internal impedance as values to be used as ERI triggering criteria, these are not believed to be the only values which may be used, and it is believed that others may be advantageously incorporated into the present invention, either in place of or in addition to those described herein.

It is contemplated by the inventors that various alterations, substitutions, and modifications, including but not limited to those specifically discussed hereinabove, may be made to the disclosed embodiments of the invention without departing from the spirit and scope of the present invention as defined in the appended claims, which follow.

What is claimed is:

1. An apparatus for indicating when a battery's depletion level exceeds a predetermined maximum, comprising:

a first monitoring circuit, coupled to said battery and adapted to periodically assess a first condition of said battery known to reflect said battery's depletion level, and to periodically generate at least one first condition signal indicative of said first condition;

a first comparison circuit, coupled to said first monitoring circuit and responsive to said at least one first condition signal to assert a first comparison signal when said first condition signal indicates that said first condition reflects a level of battery depletion greater than said predetermined maximum;

a second monitoring circuit, coupled to said battery and to said first comparison circuit, said second monitoring circuit responsive to said assertion of said first comparison signal to assess a second condition of said battery known to reflect said battery's depletion level, and to generate at least one second condition signal indicative of said second condition;

a second comparison circuit, coupled to said second monitoring circuit and responsive to said at least one second condition signal to assert a second comparison signal when said second condition signal indicates that said second condition reflects a level of battery depletion greather than said predetermined maximum;

an accumulator circuit, coupled to said second comparison circuit and responsive to assertion of said second comparison signal to increment an accumulator value;

a depletion indicator circuit, coupled to said accumulator circuit and adapted to assert a depletion indicator signal when said accumulator value exceeds a predetermined maximum, said depletion indicator circuit further adapted to periodically reset said accumulator value.

2. An apparatus in accordance with claim 1, wherein said first condition is said battery's loaded terminal voltage and wherein said second condition is said battery's internal impedance.

3. A method of indicating when a battery has reached a predetermined level of depletion, comprising the steps of:

(a) assessing at least one condition of said battery known to reflect said battery's depletion level;

(b) incrementing an accumulator value when said at least one condition assessed in step (a) reflects a depletion level greater than said predetermined level of depletion;

(c) repeating steps (a) and (b) once each time a first predetermined time interval elapses;

(d) resetting said accumulator value to zero once each time a second predetermined time interval, greater than said first predetermined time interval, elapses;

(e) asserting a depletion indicator signal when said accumulator value exceeds a predetermined maximum level.

4. A method in accordance with claim 3, wherein said first predetermined time interval is three hours and wherein said second predetermined time interval is twenty-four hours.

5. A method in accordance with claim 4, wherein said step of incrementing comprises adding sixty-four to said accumulator value and wherein said predetermined maximum accumulator value level is 255.

6. A method in accordance with claim 5, wherein said at least one condition includes said battery's loaded terminal voltage and said battery's internal impedance level.

7. An apparatus for indicating when a battery's depletion level exceeds a predetermined maximum, comprising:

a monitoring circuit, coupled to said battery and periodically obtaining a measured value of a characteristic of said battery, where said characteristic is known to reflect said battery's depletion level, and periodically generating signals corresponding to said measured values;

a low-pass filter circuit, coupled to said monitoring circuit, receiving said measured values, and digitally filtering them to yield filtered values;

an indicator circuit, coupled to said low-pass filter circuit, responsive to assert an indicator signal when said filtered value exceeds a predetermined maximum value.

8. An apparatus in accordance with claim 7, wherein said characteristic of said battery is said battery's loaded terminal voltage.

9. An apparatus in accordance with claim 7, wherein said characteristic of said battery is said battery's internal impedance.

10. An apparatus for indicating when a battery's depletion level exceeds a predetermined maximum, comprising:

a depletion monitoring circuit, coupled to said battery and adapted to periodically generate a digital output value reflecting a level of a characteristic of said battery known to reflect said battery's depletion level;

a low-pass filtering circuit, coupled to said depletion monitoring circuit and adapted to perform a digital low-pass filtering operation on a plurality of said periodically generated digital output values to produce a filtered value;

an indicator circuit, coupled to said low-pass filter circuit and adapted to assert an indicator signal when said filtered value exceeds a predetermined threshold.

11. An apparatus for indicating when a battery's depletion level exceeds a predetermined maximum, comprising:

a voltage measurement circuit, coupled to said battery and adapted to periodically measure said battery's loaded terminal voltage and to periodically generate a first digital output value;

a first comparator circuit, coupled to said voltage measurement circuit and adapted to assert a first comparator signal when said periodically generated first digital output value is below a predetermined minimum voltage;

an impedance measurement circuit, coupled to said battery and to said first comparator circuit, said impedance measurement circuit responsive to said assertion of said first comparator signal to measure said battery's internal impedance, and to generate a second digital output value corresponding to said measured battery loaded terminal voltage;

a second comparator circuit, coupled to said impedance measurement circuit and adapted to assert a second comparator signal when said second digital output value exceeds a predetermined maximum value;

an accumulator circuit, coupled to said second comparator circuit and responsive to said assertion of said second comparator signal to increment an accumulator value;

an indicator circuit, coupled to said accumulator circuit and adapted to assert an indicator signal when said accumulator value exceeds a predetermined maximum.

12. An apparatus for indicating when a battery reaches a predetermined level of depletion, comprising:

a voltage measurement circuit, coupled to said battery and adapted to generate voltage signals representing a measured value of said battery's loaded terminal voltage once each time a first predetermined time interval elapses;

an averaging circuit, coupled to said voltage measurement circuit and responsive to said generation of said voltage signals to update a running average of measured loaded terminal values;

a comparison circuit, coupled to said voltage measurement circuit and adapted to assert a first threshold signal when said voltage signals represent a loaded terminal voltage below a predetermined minimum voltage;

said voltage measurement circuit being responsive to assertion of said first threshold signal to generate voltage signals representing a measured value of said battery's loaded terminal voltage once during each of a plurality of second predetermined time intervals, wherein said second predetermined time intervals are shorter than said first predetermined time intervals;

said comparison circuit being further adapted to assert a second threshold signal during one of said plurality second time intervals when said running average of measured loaded terminal values is below said predetermined minimum voltage.

13. A method of indicating when a battery reaches a predetermined depletion level, said method comprising the following steps:

(a) measuring said battery's loaded terminal voltage;

(b) after each measurement in step (a), updating a running average of loaded terminal voltage measurements;

(c) comparing each measurement from step (a) to a predetermined minimum loaded terminal voltage;

(d) repeating steps (a) through (c) at a first periodic rate until said comparison step (c) above indicates that said measurement from step (a) is below said predetermined minimum voltage;

(e) repeating steps (a) and (b) after said comparison step (c) above indicates that said measurement from step (a) is below said predetermined minimum voltage;

(f) comparing said updated running average to said predetermined minimum loaded terminal voltage;

(g) asserting an indicator signal when said comparison in step (f) above indicates that said running average is below said predetermined minimum loaded terminal voltage;

(h) repeating steps (e) through (g) above a predetermined number of times at a second periodic rate, faster than said first periodic rate;

(i) after said step (h) of repeating a predetermined number of times, repeating step (d).

* * * * *